(12) United States Patent
Merritt

(10) Patent No.: US 9,458,024 B2
(45) Date of Patent: Oct. 4, 2016

(54) POLYGENERATION PRODUCTION OF POWER AND FERTILIZER THROUGH EMISSIONS CAPTURE

(71) Applicant: Grannus LLC, Tucson, AZ (US)

(72) Inventor: James Kelly Merritt, Katy, TX (US)

(73) Assignee: Grannus LLC, Tucson, AZ (US)

( * ) Notice: Subject to any disclaimer, the term of this patent is extended or adjusted under 35 U.S.C. 154(b) by 24 days.

(21) Appl. No.: 14/406,020

(22) PCT Filed: Jun. 21, 2013

(86) PCT No.: PCT/IB2013/002045
§ 371 (c)(1),
(2) Date: Dec. 5, 2014

(87) PCT Pub. No.: WO2014/001917
PCT Pub. Date: Jan. 3, 2014

(65) Prior Publication Data
US 2015/0291438 A1    Oct. 15, 2015

Related U.S. Application Data

(60) Provisional application No. 61/665,069, filed on Jun. 27, 2012.

(51) Int. Cl.
*C01C 1/04*    (2006.01)
*C01B 3/02*    (2006.01)
(Continued)

(52) U.S. Cl.
CPC ............. *C01C 1/0488* (2013.01); *C01B 3/025* (2013.01); *C01B 3/36* (2013.01); *C01B 2203/025* (2013.01); *C01B 2203/044* (2013.01);
(Continued)

(58) Field of Classification Search
CPC ........... C01B 3/02; C01B 3/025; C25B 1/02; C25B 1/04; C01C 1/04; C01C 1/0488; B01B 21/087; C07C 273/10
See application file for complete search history.

(56) References Cited

U.S. PATENT DOCUMENTS 4,320,103 A    3/1982    Pagani
4,671,893 A    6/1987    Pinto
(Continued)

FOREIGN PATENT DOCUMENTS

EP    1765732 B1    9/2014
EP    2817260 A1    12/2014
(Continued)

OTHER PUBLICATIONS

Edward S. Rubin et al.; Development and Application of Optimal Design Capability for Coal Gasification Systems; Technical Documentation: Oxygen-based Combustion Systems (Oxyfuels) with Carbon Capture and Storage (CCS); Work Performed Under Contract No. DE-AC21-92MC29094, Reporting Period Start, Oct. 2003, Reporting Period End, May 2007; Report submitted May 2007.
(Continued)

*Primary Examiner* — Anthony J Zimmer
(74) *Attorney, Agent, or Firm* — Dentons US LLP

(57) ABSTRACT

Method for the productioii of ammorsia, and optionally urea, from a flue gas effluent from an oxygen-fired, process, wherein the production of ammonia and optionally urea includes a net power production. Also provided is a method to effect cooling in an oxygen-fired process with air separation unit exit gases utilizing either closed or open cooling loop cycles.

18 Claims, 1 Drawing Sheet

(51) Int. Cl.
  *C01B 3/36*  (2006.01)
  *C07C 273/10*  (2006.01)
(52) U.S. Cl.
  CPC  *C01B 2203/047* (2013.01); *C01B 2203/0415* (2013.01); *C01B 2203/0475* (2013.01); *C01B 2203/068* (2013.01); *C01B 2203/1235* (2013.01); *C01B 2203/147* (2013.01); *C07C 273/10* (2013.01); *Y02P 30/30* (2015.11)

(56) References Cited

U.S. PATENT DOCUMENTS

| | | | |
|---|---|---|---|
| 4,690,812 | A | 9/1987 | Ranke et al. |
| 4,869,887 | A | 9/1989 | Van Dijk |
| 5,076,837 | A | 12/1991 | Rathbone et al. |
| 5,185,139 | A | 2/1993 | Krishnamurthy et al. |
| 6,011,073 | A * | 1/2000 | Agee .............. C01B 3/042 422/211 |
| 6,231,827 | B1 | 5/2001 | Pagani et al. |
| 6,340,451 | B1 | 1/2002 | Pagani et al. |
| 6,696,026 | B2 | 2/2004 | Pagani et al. |
| 7,470,415 | B2 | 12/2008 | Davey et al. |
| 8,012,446 | B1 | 9/2011 | Wright et al. |
| 2002/0055545 | A1* | 5/2002 | Sheppard .............. C07C 1/0485 518/702 |
| 2004/0028595 | A1 | 2/2004 | Davey et al. |
| 2007/0256361 | A1 | 11/2007 | Kindig |
| 2008/0134666 | A1 | 6/2008 | Kulkarni et al. |
| 2009/0064582 | A1* | 3/2009 | Malhotra .............. B01J 8/067 48/85 |
| 2009/0121191 | A1 | 5/2009 | Tillman |
| 2010/0107607 | A1 | 5/2010 | Kopp |
| 2010/0132259 | A1 | 6/2010 | Haque |
| 2010/0205856 | A1* | 8/2010 | Kubic .............. B01D 53/62 44/451 |
| 2010/0303703 | A1* | 12/2010 | Filippi .............. C01B 3/025 423/359 |
| 2011/0250119 | A1 | 10/2011 | Mello et al. |
| 2015/0014596 | A1 | 1/2015 | Filippi et al. |

FOREIGN PATENT DOCUMENTS

| | | |
|---|---|---|
| GB | 1104628 A | 12/1966 |
| WO | 03027062 A1 | 4/2003 |
| WO | 2007134075 A2 | 11/2007 |
| WO | 2009079681 A1 | 7/2009 |
| WO | 2011008900 A1 | 1/2011 |

OTHER PUBLICATIONS

Toon Van Harmelen et al.; The Impacts of CO2 Capture Technologies on Transboundary Air Pollution in the Netherlands; Reference No. BOLK; Number of pages 15 (incl. appendices), Number of appendices 4; May 2008.

Nexant Chem Systems; Multi-Client Study Prospectus, Polygeneration from Coal, Integrated Power, Chemicals and Liquid Fuels; pp. 1-45; Jul. 2008.

* cited by examiner

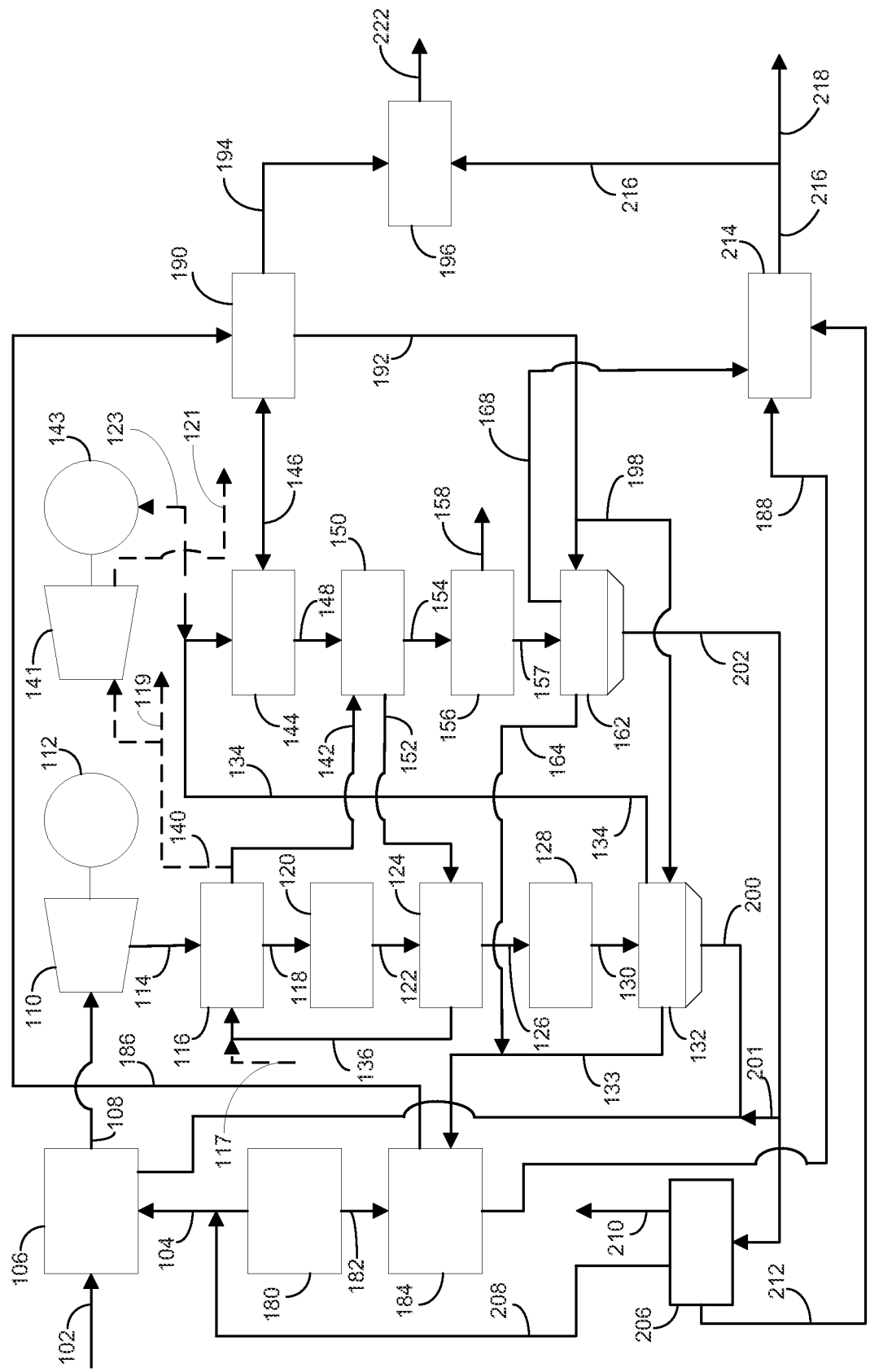

POLYGENERATION PRODUCTION OF POWER AND FERTILIZER THROUGH EMISSIONS CAPTURE

FIELD OF THE INVENTION

This invention relates to a process for the production of ammonia and/or nitrogen based fertilizers. More specifically, the invention relates to a polygeneration process for the production of ammonia and/or urea from a flue gas product stream from an oxygen-fired ("oxy-fired") industrial process, wherein the process can result in the net production of recoverable and salable power.

BACKGROUND OF THE INVENTION

Nitrogen is an important nutrient for supporting development and growth of plant life. Urea and ammonia are two common nitrogen containing compounds that are widely used in the fertilizer industry, as well as being used as basic chemicals in the production of a variety of different chemical compounds.

Ammonia is a precursor to many nitrogen containing compounds, including urea, and therefore is an important chemical to the fertilizer industry. Because of its many uses, ammonia is one of the most highly produced inorganic compounds, typically enjoying worldwide production in excess of 100 million tons. Of the ammonia produced, approximately 80% or more of the ammonia is utilized for the fertilization of agricultural crops.

Urea (or carbamide) is an organic compound having the chemical formula $NH_2CONH_2$. More than 90% of the world production of urea is for use in fertilizers as urea has the highest nitrogen content of all commonly used solid nitrogenous fertilizers. Due to the wide use of urea in fertilizers as a convenient source of nitrogen, urea production is important. Additionally, urea is an important feedstock for the manufacturing of plastics, resins, glues, and pharmaceuticals, and is also important as a feed product for ruminant animals.

Generally, industrial plants producing urea and urea based fertilizers suffer from high feedstock costs, excessive energy requirements, and high emissions. Thus, a need exists for the development of new methods for the production of urea and nitrogen based fertilizers which reduce costs and emissions.

SUMMARY

Generally, the present invention provides a polygeneration method for the production of ammonia and/or nitrogen based fertilizers, such as urea ($NH_2CONH_2$) and ammonium nitrate ($NH_4NO_2$) from the flue gas for an oxygen-fired industrial process, along with the concurrent production of energy.

In one aspect, the present invention provides a method for producing urea from exhaust flue gases of an oxygen-fired process. The method includes the steps of supplying a hydrocarbon or carbon based feedstock and oxygen to an oxygen-fired process to produce an exhaust flue gas that includes carbon dioxide, carbon monoxide, and hydrogen. The exhaust flue gas is then supplied to a first reactor, said first reactor including a catalyst and being configured to convert at least a portion of the carbon monoxide to carbon dioxide and produce a modified exhaust flue gas. The modified exhaust flue gas is then supplied to a second reactor, said second reactor including a catalyst and being configured to convert any remaining carbon monoxide to carbon dioxide to produce a carbon dioxide-rich exhaust flue gas. The carbon dioxide-rich exhaust flue gas is then supplied to a first condenser to remove water and produce a gas stream comprising primarily hydrogen and carbon dioxide. The gas stream comprising primarily hydrogen and carbon dioxide from the first condenser is supplied to a carbon dioxide stripper to produce a hydrogen stream and a high purity carbon dioxide stream; said carbon dioxide stripper may be a solvent suitably charged for extracting carbon dioxide, a mechanical separation membrane, or a mechanical pressure and/or temperature swing absorption system, and wherein the exiting hydrogen stream includes minor amounts of carbon monoxide and carbon dioxide. The hydrogen stream is supplied to a third reactor, said third reactor including a catalyst and being configured for the production methane from the minor amounts of carbon monoxide and carbon dioxide present in the hydrogen stream, said third reactor producing a methane product stream and a high purity hydrogen stream. The high purity hydrogen stream and nitrogen gas are supplied to a fourth reactor, said fourth reactor including a catalyst and being configured to produce an ammonia product stream. The high purity carbon dioxide stream and the ammonia are then supplied to a fifth reactor, said fifth reactor being configured to produce a product stream comprising urea.

BRIEF DESCRIPTION OF THE DRAWINGS

FIG. 1 shows one embodiment of a process for the production of ammonia and/or urea.

DETAILED DESCRIPTION OF THE INVENTION

Although the following detailed description contains many specific details for purposes of illustration, it is understood that one of ordinary skill in the art will appreciate that many examples, variations and alterations the process and apparatus herein are within the scope and spirit of the invention. Accordingly, the exemplary embodiments of the invention described herein are set forth without any loss of generality, and without imposing limitations, on the claimed invention.

The process described herein provides a polygeneration process for the combined production of urea and nitrogen based fertilizer from the by-products of an oxygen-fired power generation or oxygen-fired industrial process. As used herein, "polygeneration" refers to an integrated process that has three or more outputs, which includes energy output(s), produced from one or more input resources. The oxygen-fired power generation or oxygen-fired industrial process generates a hot gaseous stream (i.e., flue gas) consisting of core gases of carbon monoxide, carbon dioxide, and hydrogen, which can then be supplied to the ammonia and/or fertilizer production steps. In certain embodiments, the flue gas can be supplemented with cold nitrogen, which has not been supplied to hot gas process, to produce nitrogen and ammonia-based fertilizer as byproducts of the power generation or industrial gas process.

A variety of known oxygen-fired, zero-emission power generation schemes have been proposed in the past, such as the Matiant and Graz cycles, and can be advantageously used in the present invention for providing a feedstock for the preparation of the ammonia and urea compounds. For example, the schemes proposed in U.S. Pat. Nos. 5,715,673 and 5,956,937 are based on a process in which a high-pressure combustor is fired with oxygen, gaseous fuel, and water to produce a drive gas for a steam turbine. The discharge from the turbine can be reheated in an intermediate pressure combustor fired with additional fuel and oxygen. The discharge then enters a turbine to generate additional power. The discharge can be supplied to a condenser to separate water, and a carbon dioxide-rich effluent can then be vented, compressed, treated, and sold or delivered to a sequestration site.

Another method for operating a boiler using oxygen-enriched oxidants is disclosed in U.S. Pat. No. 6,314,896; which generally discloses a method for operating a boiler in which oxygen-enriched air is introduced with a fuel into the combustion space within a steam-generating boiler.

Another exemplary scheme for power generation using steam and gas turbines that can be used was proposed by Bolland and Saether (see, ENERGY CONVERSION & MANAGEMENT, Vol. 33, Nov. 5-8, 1992, p. 467). The scheme consists of supplying a combustor with oxygen from an air separation unit (also referred to as an "ASU"), reacting the oxygen with fuel, adding water or steam to control combustor outlet temperature, and passing combustor gases through a turbine to generate power. In this heat recovery system, a water inlet stream is used to cool the discharge of the air separation unit main compressor.

Yet another scheme that was proposed discloses using oxygen-fired combustion in conjunction with a water recycle (see, Yantovskii; PROCEEDINGS OF WORLD CLEAN ENERGY CONFERENCE, Geneva, Switzerland, 1991, pp. 571-595). A high-pressure combustor receives oxygen from an air separation unit, hydrocarbon fuel, and recycled water to produce a steam/carbon dioxide drive gas that enters a turbine. This is followed by two stages of reheating and expansion. The carbon dioxide is separated in a condenser, and the condensate is recycled to the high-pressure combustor. The cycles described are purportedly capable of attaining relatively higher efficiencies, but this is contingent upon the development of advanced steam turbines.

In a process known as the "Matiant" cycle, (see, PROCEEDINGS OF THIRD INTERNATIONAL CONFERENCE ON CARBON DIOXIDE REMOVAL (ICCDR-3), Boston, 1996), a drive gas for a gas turbine is produced by combusting with oxygen and recycled carbon dioxide. The drive gas enters a turbine operating at pressures and temperatures characteristic of gas turbines. The turbine discharge enters a heat recovery device, such as a heat recovery steam generator, is cooled, and the water is separated. A portion of the carbon dioxide-rich effluent is recycled to the combustor and the remainder is vented or compressed. Variations of this concept also incorporate techniques to liquefy, heat, and expand the carbon dioxide product, as disclosed, for example, in U.S. Pat. No. 5,802,840. Similar schemes are also described in U.S. Pat. Nos. 3,736,745; 4,434,613; 4,498,289; 5,175,995; 5,247,791; and 5,265,410.

Although these cycles purport to enable higher efficiency energy production, they are dependent on the development of increasingly high pressure, high temperature turbines which are not currently available.

An exemplary scheme for the production of power is through "Isothermal Gas Turbine Using Catalytic Partial Oxidation" in International Patent WO 91/05946, May 2, 1991(J.S. Ribesses) and demonstrated by the Institute of High Temperature (1VTAN) in the former Soviet Union in the late 1950s. This scheme demonstrated catalytic partial oxidation reactors and combustion of the gas through partial oxidation gas turbines to generate power without contemplation of fertilizer production. Later and current work by the Gas Turbine Institute ("GTI") building on this concept has shown potential for hydrogen production and Fischer-Tropsche gas-to-liquids applications from a slip stream of the synthesis gas, but did not contemplate synthesis of ammonia based fertilizers and urea (Newby, et. al, "An Evaluation of a Partial Oxidation Concept for the Combustion of Turbine Power Systems." ASME paper 97-AA-24, 1997). The similar scheme as described in U.S. Pat. No. 8,268,896 was the resulting work of the previous concepts, but requires emissions to atmosphere of contaminant gases such as nitrous oxides, use of natural air or oxygen amended air flow for fuel oxidation, and does not provide for economic or innovative capturing and reuse of carbon dioxide. Embodiments of the present invention provide apparatus and processes that operate with an oxygen atmosphere to remove contaminant gases, have higher economic efficiency for the production of synthesis gas, use flue gas for ammonia production with bypassed nitrogen, and provide a means to capture and reuse carbon dioxide and nitrogen in the production of fertilizer.

In contrast to the Matiant cycle, the "Graz Cycle" (see, ASME paper 95-CTP-79, ASME COGEN-TURBO POWER CONFERENCE, Vienna, Austria (1995), and also in CIMAC paper G07, CIMAC CONFERENCE, Interlaken, Switzerland (1995)) describes a high-pressure combustor fired with fuel, oxygen, steam, and a recycled carbon dioxide steam. The stream leaving the combustor is expanded in a high-pressure turbine and enters a heat recovery system to generate pure steam, which subsequently enters a steam turbine. The discharge from the steam turbine then enters the combustor. After heat recovery, a portion of the high pressure turbine discharge is compressed and recycled back to the combustor while the remaining portion enters a low pressure turbine and a water removal system.

In one aspect, a method for the production of ammonia and/or urea from the exhaust gases of an oxygen-fired process is provided. In the method, a hydrocarbon fuel source, such as methane or syngas, supplied via line 102 and oxygen supplied via 104 are combined in oxygen-fired industrial process 106 to produce an exhaust flue gas. The exhaust flue gas can be supplied via line 108 to power turbine 110, which removes a portion of the heat and produces energy with power generator 112 connected thereto. Other hydrocarbon fuels and byproducts such as tar, pitch, bitumen, coal, petcoke, or like materials that are able to be oxidized in an oxygen-fired process and that can be subjected to cleanup or contaminant removal can be used as feedstock, however, these alternate fuels require certain removal systems for contaminants contained therein. Other hydrocarbon fuels heat transfer mechanisms may include a boiler (heat exchanger) with a secondary steam cycle or high contaminant turbine to transfer the energy of the flue gas and pass the exhaust via line 114 to the first heat exchanger 116. Exemplary contaminant removal systems can include sulfur removal systems, such as a wet limestone scrubber, ash using a baghouse, or electrostatic precipitator, and candle filters for the removal of metals, each of which can be added to the flue gas treatment stream. For example, a flue gas wet scrubber could replace the first condenser for water removal and polishing the water prior reintroduction to the combustion cycle or sale. Each of these flue gas treatments for systems employing other hydrocarbons can also create salable byproducts to the process. For example, acid gas removal systems for sulfur will produce elemental sulfur, which is beneficial to the treatment of fertilizer for extended release breakdown of the fertilizer. Trace amounts of nitrogen can be scrubbed in the process and converted to nitrogen or ammonia.

Exhaust flue gases exit turbine 110 at high temperature, typically at a temperature that is greater than about 475° C., alternatively between about 410 and 500° C., alternatively about 495° C., via line 114, and include a mixture of carbon monoxide, hydrogen, carbon dioxide, oxygen, water (for example, as steam), and inert gases. In certain embodiments, the gas mixture can include between about 55 and 65 mol. % hydrogen, 15-25 mol. % carbon dioxide, and between 10 and 20 mol. % carbon monoxide. In an alternate embodiment, the gas mixture can include between about 60 and 65 mol. % hydrogen, between 17 and 23 mol. % carbon dioxide, and between 10 and 15 mol. % carbon monoxide. The exact ratio of the exhaust flue gas depends on the exact composition of the fuel source (i.e., methane, syngas, or other hydrocarbon source) and upon the stoichiometric balance of oxygen and fuel supplied to the oxygen-fired process.

Conversion of carbon to mostly carbon monoxide and carbon dioxide and hydrogen to water is possible in a stoichiometric balance or an excess oxygen environment at line 114. In certain embodiments, a 3:1 ratio of hydrogen to carbon dioxide will be achieved at line 114. When the ratio of hydrogen to carbon dioxide is less than 3:1, as evidenced by a lack of free hydrogen at line 114, and as also seen by the amount of hydrogen produced at line 168, additional make-up hydrogen can be supplied by hydrogen generator 206 via line 212 to the ammonia production process in reactor 214 and additional oxygen can be supplied to oxygen-fired industrial process 106 via lines 104 and 208. In certain embodiments, the process does not limit the ratio of carbon dioxide:hydrogen within these limits, but they are preferred for optimized production and efficiency. Not all embodiments will require the hydrogen generator as a source of hydrogen; the source of hydrogen can come from other industrial sources when the hydrogen supply is not adequate for a 3:1 ratio. The addition of hydrogen from a hydrogen generator can provide additional hydrogen, as needed to produce the desired carbon dioxide:hydrogen ratio entering the process cycle for production of ammonia. In certain embodiments, the fuel flow can control the production of carbon-oxides entering the system in stoichiometric balance or un-balance with oxygen entering the process. In certain embodiments, a fuel-rich, oxygen-lean process may result in uncombined carbon being formed. Uncombined carbon can foul the system as carbon black or coke, therefore oxygen and fuel ratio needs to be controlled to prevent or minimize uncombined carbon. The oxygen-fired process can be modified to optimize the ratio of flue gases for highest efficiency and desired flue gas ratios. Oxidized hydrogen from the flue gas will produce water, which can be supplied from the condenser to the hydrogen generator for production of hydrogen, injected into the fourth reactor via line 212, returning the chemical balance back to a ratio to support the production of ammonia.

Exhaust flue gases in line 114 can optionally be supplied to first heat exchanger 116 to control the temperature of the gases for further processes. When the fuel source is synthesis gas supplied, for example, by an integrated gasification cycle, carbon dioxide produced from the synthesis gas fuel as a byproduct can be injected into the carbon dioxide line 194, if the carbon dioxide is pure, or into line 114 if the carbon dioxide is not pure and further treatment is needed for carbon monoxide and carbon dioxide clean-up. First heat exchanger 116 can be of any type known in the art, such as steam generator. The size of first heat exchanger 116 can be selected based upon the cooling required to reduce the temperature of the exhaust flue gases in line 114. The exhaust flue gases exiting first heat exchanger 116 supplied via line 118 to first reactor 120, which can include a water-gas shift reaction catalyst. The exhaust flue gases exit first heat exchanger via line 118 at a temperature selected based upon the first reactor catalyst requirements. For example, in certain embodiments, the first heat exchanger can be configured, to reduce the temperature of the exhaust flue gases in line 114 to less than about 400° C., alternatively less than about 375° C., alternatively between about 355° C. and 365° C.

For example, in one embodiment of the Haber-Bosch process, the catalyst in the first reactor can include $Cr/Fe_3O_4$, requiring an inlet temperature of the flue gas of about 360° C. It is understood that one of skill in the art may select alternate catalysts for the various reactors described herein, which may require a different input temperature. In embodiments employing the Haber-Bosch process, the catalyst present in first reactor 120 converts carbon monoxide to carbon dioxide via a water gas shift reaction: 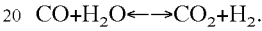

A gas stream exiting first reactor 120 can be removed via line 122 and supplied to second heat exchanger 124. The gas stream can include carbon monoxide, water, carbon dioxide and hydrogen gases. In certain embodiments, second heat exchanger 124 can reduce the temperature of the gases to less than about 250° C., alternatively less than about 225° C., alternatively to between about 205° C. and 215° C., depending upon the specifications of the catalyst in second reactor 128.

Steam or hot water supplied via line 136 from second heat exchanger 124 can be heated in first heat exchanger 116 while reducing the temperature of turbine exhaust gases exiting turbine 110 via line 114. Make up steam or water can be provided to the process via line 117, and can be supplied from an associated process. Steam discharged from first heat exchanger 116 via line 142 to third heat exchanger 150 can then be supplied via line 152 to second heat exchanger 124 to cool gases entering second reactor 128. Excess steam from first heat exchanger 116 can be supplied via line 140 and used to drive an auxiliary turbine generator 141 and/or an auxiliary compressor 143. Alternately, excess steam removed via line 140 can be removed from the system to provide heating for an associated process via line 119.

Auxiliary turbine 141 can be coupled to and drive compressor 143, which can be utilized for required gas compression loads. In certain embodiments, a motor-generator can be attached to the same compressor shaft and operate as a motor for start-ups and shutdowns. Steam supplied via line 140 can be used to convert the motor to a generator as supply pressure overcomes the load of the compressor, unloading the motor, and eventually supplying enough torque to run both the compressor and motor as a compressor and generator. In certain embodiments, motor-generator can include slip rings and brushes or a permanent magnet generator for the field magnetism. In certain larger installations, multiple turbine units and motors can be used to meet redundancy requirements. Once redundancy requirements are met for start-up and shutdown reliability, a turbine-generator or turbine-compressor may be added to provide power generation or gas compression with excess steam. As is understood by one of skill in the art, not all turbine shafts will include motor-generator drives. The motor-generator drive advantageously facilitates the start-up and shutdown processes, and can reduce both the cost of the equipment and the number of shafts needed per piece of equipment. In certain embodiments, saturated steam can be removed from auxiliary turbine 141 and supplied to a condenser, or to an associated process. Carbon dioxide can be supplied from line 134 via line 123 for compression by compressor 143, and supplied to the carbon dioxide removal process 144 via a parallel line at 123. A load control valve between lines at 134 and 123 will select the load of the compressor if needed and cycle the compressor into service mode, modulate mode, and out of service (unloaded). Some embodiments may not have need for the compressor if backpressure turbines and condensers are used for turbine 110 and condenser 132, and if the pressure is adequate to provide flow into carbon dioxide removal process 144 via line 134 directly. Optionally, steam can also be released via steam outlet 121.

Gases exiting first reactor 120 via line 122 are supplied to second heat exchanger 124 to control the temperature of the gases, and then supplied via line 126 to second reactor 128. In certain embodiments, the second reactor 128 can include a catalyst operable to scavenge remaining carbon monoxide in the water gas shift, such as by the Haber-Bosch process. In embodiments employing the Haber-Bosch process, the catalyst in second reactor 128 can include Cu/ZnO/Cr and can be supplied to the reactor at a temperature of about 210° C. The Haber-Bosch process converts any remaining carbon monoxide in the gas to carbon dioxide in a water gas shift reaction, $CO + H_2O \leftrightarrow O_2 + H_2$.

The gas mixture produced in second reactor 128 exits via line 130 and can be supplied to condenser 132. Generally, the gases exiting second reactor 128 will be saturated with water vapor. The water vapor condensed in condenser 132, which is cooled by chilled water supplied via line 198, which itself can be cooled by various means, such as with gases (e.g., nitrogen) provided by air separation unit 180. In certain embodiments, the nitrogen gas from air separation unit 180 can be supplied to nitrogen gas heat exchanger 184 via line 182, having a temperature of between about 4-21° C., or in some embodiments 10-40° C., as necessary to facilitate the condensation of water from the produced gases. Condensate water removed from condenser 132 via line 200 can be supplied to oxygen-fired process 106, to the hydrogen generator 206, to the heat exchangers, to excess water sales, or to an associated process for urea production, such as granulation or prilling. Water from condenser 132 can also be fed via line 133 to the nitrogen gas heat exchanger 184.

Urea product is concentrated in three different methods in the art, by vacuum concentration, crystallization, or atmospheric evaporation. To prill, a concentrated urea solution called "melt" is admitted to an evaporator to reduce moisture content. The resulting molten urea is pumped to spray nozzles of a tower and passed counter flow to air current. Prill is formed as urea droplets combine and fall through the tower and cool. Two primary processes are currently used in the art utilizing fluidized bed and non-fluidized bed prill towers. For granulation, molten urea is sprayed into a drum or pan having seed granules sieved from the output of the process. The rotation of the drum or agitation of the pan allows for product layering and coating, and for the combination with other products, such as clay, phosphates, or sulfur. The byproduct of both granulation and prilling is sieved for size and the small product is recycled to in the process. Granules of proper size are collected for storage and byproduct delivery.

Gas vapors exiting condenser 132 via line 134 through air separation baffles will primarily include a ratio of hydrogen and carbon dioxide, possibly also including small or trace amounts of carbon monoxide and inert gases. In certain embodiments of the Haber-Bosch process, the gas ratio is about 74% hydrogen, 24% carbon dioxide, 2% carbon monoxide, and trace inert gases. Gas supplied via line 134 is supplied to carbon dioxide removal unit 144. In certain embodiments, it may be necessary to have a vacuum pump or compressor 143 present in carbon dioxide removal line 134 to extract gases from the condenser baffles and discharge to the carbon dioxide removal process 144 if a vacuum in the condenser 132 due to the collapse of the volume of steam to water. In backpressure type turbines if selected in the art to match the turbine design parameters, the carbon dioxide rich gas flow may not require the compressor to transfer gas from the condenser to the next stage of carbon dioxide removal process due to maintained positive pressure in the condenser. Carbon dioxide removal unit 144 removes carbon dioxide using an extraction media supplied, such as an amine based solutions, such as MDEA (methyldiethanolamine), MEA (monoethanolamine), Ucarsol™, DGA (diglycolamine) and the like. In certain embodiments, carbon dioxide removal process 144 can employ the Rectisol™ removal process. In certain embodiments, mechanical separation, water wash, or pressure/temperature swing adsorption may be used to separate the hydrogen and carbon dioxide streams at unit 144. The carbon dioxide is then recovered in carbon dioxide recovery unit 190, which separates the amine based extraction media from the carbon dioxide. The carbon dioxide-lean amine based extraction media can then be recycled via line 146 to carbon dioxide removal unit 144, which can cycle the extraction media in a rich and lean process loop. The amine can be condensed with chilled water from the chill water system flow supplied via line 186, which exits from carbon dioxide recovery unit 190 via line 192. A high purity carbon dioxide stream can then be supplied to fifth reactor 196 via line 194, or alternatively can be recovered or supplied to an alternate associated process (not shown). Line 192 can be split via a splitter to form chilled water line 198, which is fed to condenser 132.

Hydrogen gas having a purity of greater than 95%, preferably at least about 99%, and including uncaptured carbon dioxide and carbon monoxide, exiting the carbon dioxide stripper 144 is supplied via line 148 to third heat exchanger 150, wherein the gases can be heated to a desired temperature and supplied via line 154 to third reactor 156, wherein the third reactor includes a catalyst suitable for the production of methane (i.e., methanation). The temperature to which the gases are heated or cooled is selected based upon the catalyst specification for the catalyst present in third reactor 156.

Third reactor 156, which can include a catalyst suitable for the conversion of carbon monoxide to methane, converts the remaining trace amounts of carbon dioxide and carbon monoxide, along with hydrogen, into methane and water vapor. In the Haber-Bosch process, the catalyst can include $Ni/Al_2O_3$ and the gas inlet temperature can be about 325° C. The conversion generally takes place in two primary reactions, $CO + 3H_2 \rightarrow CH_4 + H_2O$ and $CO_2 + 4H_2 \rightarrow CH_4 + 2H_2O$. Methane and water produced by the reactions can be removed by gas separation (for example, by pressure swing adsorption (PSA), condensation, membrane technologies, and the like), and returned via line 158 to the inlet of the oxygen-fired process 106 as fuel gas.

Highly pure hydrogen having a purity of at least about 99.9% exiting the third reactor 156 via line 157 with any excess water is supplied to condenser 162, wherein water is condensed and removed via line 202, and the highly pure hydrogen is supplied via line 168 to fourth reactor 214 for the production of ammonia. Water is condensed from the gases supplied via line 157 through condensation with chilled water via line 192. The hydrogen gas can exit through gas separation baffles to the ammonia process via line 168. Condensate water can be supplied from line 202 to hydrogen generator 206, or supplied via lines 200 and 201 to oxygen-fired industrial process 106. Water from condenser 162 can also be fed via line 164 to the nitrogen gas heat exchanger 184. In certain embodiments, excess water can be removed from lines 200, 201, and/or 202 (not shown), as needed. Similarly, make-up water can be added to the system via lines 200, 201, and/or 202 (not shown), as needed.

Fourth reactor 214 is supplied with hydrogen gas via line 168 and line 212 if supplemental hydrogen is needed from the hydrogen generator 206 and nitrogen gas exiting the nitrogen gas heat exchanger 184 via line 188. Fourth reactor 214 includes a catalyst suitable for the production ammonia. In certain embodiments, the catalyst is an iron based catalyst, which can be promoted with potassium, calcium, and aluminum ($K_2O$, $CaO$ and $Al_2O_3$). In certain embodiments, the catalyst may be a carbon fiber based matrix with a plating in palladium, ruthenium, nickel, rhodium, or combinations thereof. In certain embodiments, hydrogen and nitrogen are supplied to the reactor and passed over the catalyst to produce ammonia via the following reaction: $N_2+3H_2 \leftrightarrow 2NH_3$. In certain embodiments, make-up hydrogen gas can be supplied to line 168 by other means (not shown), or when excess hydrogen is present, removed for sale or supply to an associated process (not shown). In certain embodiments, excess nitrogen can be vented or provided to an alternate process (not shown), or in certain embodiments, additional nitrogen can be added to the system (not shown) as needed.

Ammonia from fourth reactor 214 is supplied via line 216 to fifth reactor 196 for the preparation of urea, or extracted for collection or supply to an associated process via line 218.

Fifth reactor 196 combines ammonia having a purity of at least about 99%, preferably at least about 99.9%, supplied via line 216 and carbon dioxide having a purity of at least about 99%, preferably at least about 99.9%, supplied via line 194 to produce urea by the following reaction: $2NH_3 + CO_2 \leftrightarrow NH_2COONH_4 \leftrightarrow NH_2CONH_2 + H_2O$. In the reaction for the production of urea, for each mole of urea that is formed, one mole of water is also produced. This water produced as a by-product of the urea synthesis, can be removed (not shown) and sold or supplied to an associated process. Urea product can be sent via line 222 for collection or further processing, for example prilling and granulation.

In certain embodiments, the nitrogen can be supplied from the air separation unit, which also supplies the oxygen for the oxygen-fired process. In certain embodiments, the oxygen-fired process product flue gas can have a ratio of hydrogen:carbon dioxide of between about 2:1 and 4:1, alternatively between about 2.5:1 and 3.5:1. In certain embodiments the ratio is between about 2.9:1 and 3.1:1, alternatively about 3:1.

In certain embodiments, a 3:1 ratio of hydrogen:carbon dioxide may be desirable for further separation of element gases to make urea ($NH_2CONH_2$). Certain design and fuel parameters of the oxygen-fired generation or industrial process may require a balanced stoichiometric ratio in the flue gas and therefore require supplemental hydrogen to be added to the ammonia making process, which is a precursor to making ammonia based fertilizer. By controlling the supplementing of certain components of the flue gases, it is possible to achieve the desired or necessary ratio of gases. Feedstock for the production of hydrogen can include recycled process water, condensate water from the ammonia and fertilizer production process, connate water, fresh water, saltwater, brine, desalinated water, deionized water, or deionized brine. The process can include the use of an air separation cold box for the cooling of the heat sinks. The cooling can be provided by gases, such as nitrogen or oxygen that can chill media passing through the heat exchanger. Subsequently, the chilled media can be recycled in a closed or open loop cycle to remove heat from heat sinks within the process, such as condensers, and the bearing oil coolers of the turbines and pumps. The media can have a flowrate that can be controlled through other heat exchangers to reduce process temperatures, such as to produce condensate water or to adjust the temperature of one or more streams being supplied to a reactor. The media in the chill system loop can be liquid or gaseous, as known in the art. In certain embodiments, it can be possible to use the gas flow existing from the cold box portion of the air separation unit as the chilling media described herein, rather than using intermediary fluid(s).

As noted above, in certain embodiments of the present invention, a major advantage of the invention described herein is the replacement of the steam reformation process for the conversion of methane and synthesis gases to ammonia and/or nitrogen and ammonia based fertilizers. The use of an oxygen-fired power generation or oxygen feed industrial process provides a mechanism to the following. In certain embodiments, the system provides for the production of energy through oxygen-fired power generation and oxygen-fired industrial gasification of the feedstock to synthesis gas, and eliminates or significantly reduces the production of nitrous oxides prior to the production of nitrogen and ammonia based fertilizers. Advantageously, the energy produced can then be sold to offset the cost of feedstock with net power sales. Additionally, the use of an air separation unit advantageously allows the cold exiting gases to be used as a heat sink in various associated heat exchangers and condensers while providing nitrogen to the ammonia process and oxygen to the oxygen-fired process. Additionally, the use of the air separation unit and various heat exchangers provides a method to provide cooling to the power plant and associated industrial processes in environments having a reduced availability of cooling water, or in hot climates.

Exemplary integrated gasification combined cycle ("IGCC") oxygen-fired processes which rely on amine separation of carbon dioxide and mechanical or solvent separation of other flue gas components to provide a nitrogen-free flue gas include those provided by the following vendors; AlterNRG, Shell, GE/Texaco, British Gas/Lurgi, Destec Energy, ABB, Hitachi, VEW Steinmueller, Mitsubishi Heavy Industries (MHI), Prenflo/Uhde Deutsche-Babcock, and Noell/GSP. These exemplary TGCC systems use heat assisted direct gasification of solids to synthesis gas followed by amine and mechanical separation of flue gas constituents of nitrogen and. sulfur oxides and power generation in a separated steam system and secondary combustion of synthesis gas through a gas turbine. This IGCC technology cannot achieve greater than 90% carbon dioxide removal efficiency without mechanically choking the gas turbine. Embodiments of the present invention provided do not re-combust the flue gas after the oxygen-fired process and pass all carbon dioxide through the process. In certain embodiments, operation of a solid fuel gasification unit in stoichiometric or substoichiometric conditions may provide the flue gas (synthesis gas) necessary for the ammonia process, but excess energy for heat and steam production would be required for the gasification reaction vessel and the efficiency advantage of embodiments described herein would not be realized with additional flue gas treatment systems. Exemplary oxygen-fired turbines for use herein include, but are not limited to:

Pratt & Whitney Rocketdyne; Siemens SGT-900(formerly Westinghouse W251); Clean Energy Systems J79; GasPlas AS; and. those described in U.S. Pat. Nos. 5,715,673 and 5,956,937.

In certain embodiments, the apparatus and. process described herein can include polygeneration looping for the production of additional power and heat. In certain embodiments, the process can include integration with known ammonia and fertilizer production processes to utilize the power generation byproducts for the production of valuable chemical intermediates and products, such as sulfur, ammonia, nitrogen, hydrogen, noble gases, and rare earth metals, in certain embodiments, the feedstock for the process can be a fossil fuel or synthesis gas. In certain embodiments, the fossil fuel or synthesis gas can be treated, to remove various contaminants, such as with gas separation equipment, baghouses, scrubbers, catalytic reactors, chemical treatment processes, and/or candle filters to achieve the desired output gases.

In certain embodiments, a catalytic or non-catalytic partial oxidation reactor which provides rich fuel, and lean oxygen, under a substoichiometric reaction and heat may provide flue gases necessary to drive a partial oxidation gas turbine generator or expansion turbine generator, which flue gases exhaust into the first heat exchanger 116 and consist dominantly of carbon monoxide, carbon dioxide, hydrogen, water, and inert gases.

In certain embodiments, an oxygen-fired boiler may provide a concentrated flue gas stream of carbon dioxide and water vapor which may be condensed for removal and which the carbon dioxide may be reacted with ammonia for urea formation and/or used for industrial purposes. In this embodiment, steam from the oxygen fired boiler would provide required heat for a hydrogen generator and water condensed from the flue gas would provide the make-up water for hydrogen production. Oxygen would still come from the air separation unit and nitrogen would bypass the combustion process and be injected into the ammonia process with hydrogen. This embodiment would shorten the Haber Bosch ammonia process to one or two stages depending on carbon dioxide purity, instead of four catalyst stages.

In certain embodiments, an oxygen-fired boiler may be operated in a fuel rich condition which produces a flue gas consisting of a synthesis gas mixture of carbon dioxide, carbon monoxide, and hydrogen when operated with methane based fuel. This flue gas can be directly exhausted to the first heat exchanger 116 and continue the modified Haber Bosch ammonia process. Other hydrocarbon fuels containing sulfur may have flue gas desulfurization installed before the first catalyst. The desulfurization process may be dry or wet limestone, solvent, or amine solution or other desulfurization methods of the art. Methods of desulfurization will promote condensate removal prior to the gas shift of carbon monoxide to carbon dioxide in the modified Haber Bosch process and may require temperature correction at the first heat exchanger 116 to promote the water gas shift reaction in catalyst 118.

In certain embodiments, torrefaction or pyrolysis of carbonaceous feedstocks in an oxygen environment can provide the heat and flue gas similar to an oxygen-fired boiler or partial oxidation reactor. Carbonaceous feedstocks include feedstocks rich in carbon. In some embodiments, the carbonaceous feedstocks include solids, liquids, or organic wastes such as digestate from biogas production. Flue gas constituents and heat can be adjusted with fuel flow, oxygen flow, and vessel residence time to make the ideal synthesis gases for entry into the first heat exchanger 116. and then follow the remaining described processes to make ammonia and urea. In certain embodiments the feedstock can be solids, liquids, or organic wastes such as digestate from biogas production. Solid wastes from torrefaction or pyrolysis will be vitrified or char and repurposed for beneficial use.

In certain embodiments, the apparatus and process described herein can reduce the flue gas treatment of nitrous-oxides by employing an air separation unit, which prevents nitrogen from being supplied to the oxygen-fired process. Nitrogen that is entrained in the feedstock can be removed by known means, such as catalytic reduction, conversion to ammonia, acid removal from condensate, or other known denitrogenation processes. The oxygen supplied to the oxygen-fired process can have a purity of at least about 95%, alternatively at least about 99%, alternatively at least about 99.5%, alternatively at least about 99.9%.

In certain embodiments, the apparatus and process described herein can provide steam for steam turbine compression, desalination, combined heating and power generation, absorption chilling, and/or industrial and generation loads.

In certain embodiments, the apparatus and process described herein can provide a cold box gas source as a cooling sink to achieve the following: reduce water consumption (as compared with evaporative cooling); reduce power losses due to air cooling in the cooling cycle, increase system stability with a constant, controllable heat sink, and improve cycle efficiency through minimum condensate depression and controlled condenser backpressure.

In certain embodiments, the apparatus and process described herein creates an ultra-low to zero-emission thermal power plant. In certain embodiments, other than start-up and shutdown venting, maintenance, equipment failure or trips, the process described herein provides no emissions from the thermal power plant. Put differently, in certain embodiments, during continuous operation the present process provides zero emissions in the generation of feedstock for power production and fertilizer.

In certain embodiments, the apparatus and process described herein reduces and repurposes industrial and greenhouse gases produced as a product of power generation into nitrogen containing chemical compounds, such as fertilizer.

In certain embodiments, the apparatus and process described herein can be utilized for the production of various forms of fertilizer that incorporate ammonia and nitrogen. In certain embodiments, the apparatus and process described herein can be configured for urea production rather than ammonium-nitrate, thereby reducing the incidence of leaching of nitrates when applied as a fertilizer. In certain embodiments, the process can include a step wherein the prill is coated with sulfur, thereby providing a product having an increased disintegration time for the urea, and minimized nitrate leaching. In certain embodiments, sulfur can be removed from the feedstock and incorporated for sulfur treatment of the urea byproduct. Alternatively, in certain embodiments sulfur can be provided for sulfur treatment of the urea byproduct.

In certain embodiments, the steam and condensate produced in the associated processes, such as urea synthesis or feedstock industrial gasification to synthesis gas, can be used to provide heating or cooling, or can be used for purposes of providing pressurization. Steam production in excess of the steam generated from the feedstock to meet the process demands for the flue gas composition can be directed to auxiliary loads and used to generate additional power and either sold for a net increase of power sales, or can be supplied to power an associated process. Net steam produced by the auxiliary loads can be recycled in the steam loop or returned to the source of the steam. In certain embodiments, the use of cogeneration processes, such as the inclusion of solar thermal, geothermal, biomass, or waste heat can be integrated with the steam flow, as in the art. Through the use of heat exchangers and recycle streams, low temperature steam or water (i.e., having a temperature of between about 40 and 300° C.) can be heated and/or pressurized beneficial levels through waste heat generated by other associated processes. Higher temperatures can be directed to the gasification process for the creation of steam, and then be sent through the turbine for power production, whereas medium and lower temperatures can generate heating or cooling effects in the thermodynamic cycle. High pressure and high temperature steams that are produced as a result of the processes described herein can be passed through the oxygen-fired process or turbine, and the low temperature and low pressure water and steam can be cycled through the steam or cooling systems. In certain embodiments, chilled loads can be serviced through process looping between the power or industrial plant, ammonia processing, fertilizer processing, and/or granulation or prilling processes.

The sale of excess power produced, or internal use of excess power that is produced, will offset the power cost normally attributed to fertilizer production process and effectively reduce the cost of feedstock and fertilizer production costs. When steam reformation is used to produce the feedstock for ammonia based fertilizers, the feedstock of natural gas typically makes up about 70-90% of the total cost to produce the fertilizers.

In certain embodiments, air is supplied to the air separation unit and nitrogen is separated prior to the oxidation process, such that pure or nearly pure oxygen is supplied to the oxidation step. As noted previously, the oxygen supplied to the oxygen-fired power generation or oxygen feed industrial process can have a purity of greater than 95%, alternatively greater than about 97%, alternatively greater than about 98%, alternatively greater than about 99%. In certain preferred embodiments, the oxygen can have a purity of greater than about 99.99%. By removing nitrogen from the oxygen prior to oxidation process, the amount of energy and scale of process equipment required to provide nitrogen in ammonia production is reduced when compared to steam reformation.

The latent heat of condensation provided by gases from the air separation cold box reduces water consumption requirements for evaporative cooling for heat loads such as steam turbines and heat exchangers. The elimination of air cooled condensers and cooling towers allows for the production of power as described herein in areas having low water resource and high ambient temperatures.

Hydrogen production if required for supplemental hydrogen can also reduce the amount of oxygen required from the oxygen generator, thereby making the oxygen generator smaller and therefore a smaller electrical load and capital cost.

Known processes or portions of known processes for the production of ammonia, such as the Haber-Bosch process, and known processes for the production of urea, such as the Stami or Uhde process, are exemplary processes that can be utilized in the present invention, using the flue gas from the oxygen-fired power generation or oxygen-fired industrial gasification process to make nitrogen and ammonia based fertilizers. A variety of ammonia and fertilizer production processes could be advantageously utilized, thereby allowing for the use of a variable flue gas ratios to produce ammonium based products, such as urea, ammonium nitrate, ammonium sulfate, and ammonium phosphate. These known Haber Bosch processes would be optimized resulting from the removal of nitrogen from the gas processing path.

In certain embodiments, the catalyst specifications will dictate adjustment of temperature, pressure, and gas ratio to meet the ideal conditions for the ammonia and fertilizer production process. For example, the process parameters will be different for the iron based catalyst, as compared with ruthenium and palladium catalysts Steam generators for heat recovery can be utilized and can provide the temperature and pressure balancing for the process gases, with the flue gas flowrate being selected based upon the power or steam demands. The amount of feedstock, oxygen, and water supplied to the reaction zone prior to entering the catalysts and oxygen content will control the stoichiometric balance. Water, gas, and steam injection can also be used to control gas and density balances with controlled feedback loops. Process looping can provide mechanisms to recycle steam in the form of waste heat and condensate to the power generation or industrial process, and between the ammonia and fertilizer process. Heat sinks and sources provide efficiency loops to condense water, and to cool and reheat gases prior to passing the gases over catalysts in the reaction zones. In certain embodiments, the chilled water that is used to cool various processes, such as for example for the removal of condensate, can receive primary cooling from nitrogen gas exiting the cold box of the air separation unit. The chilled water can be used for all chilled water requirements, and in certain embodiments can be supplemented with additional types of cooling or technologies.

In certain embodiments, ammonia can be produced by the Haber-Bosch process, wherein hydrogen and nitrogen gases are passed over an iron catalyst. Separation of hydrogen from the flue gas, concentration of the carbon-dioxide, removal of condensate, and temperature and pressure control can be performed prior to passing hydrogen over the iron catalyst and blending with nitrogen to form ammonia. Nitrogen separated by the air separation unit that bypasses the combustion process can be supplied directly to the ammonia production step. In certain embodiments, the nitrogen exiting the air separation unit can be utilized for cooling loads. In certain embodiments, excess nitrogen can be separated and sold. Alternatively, in certain embodiments, excess nitrogen can be used as a cooling medium and vented.

In one embodiment directed to the production of urea, compressed carbon dioxide is removed prior to the production of ammonia. The carbon dioxide can then be combined with the ammonia for synthesis of ammonium carbamate. Heat can be supplied from an associated process, such as urea process looping or auxiliary steam, and used to strip excess carbon dioxide and ammonia from the ammonium carbamate. Two separate recycle loops can thus be formed a first loop for the production of urea and water, and the second loop for the recycle of excess gases. Excess water can be removed, for example by evaporation, prior to the prilling or granulation process.

Exothermic reactions in the urea processes described herein, and which produce steam and/or heat, can discharge the steam to the heat recovery steam generator or auxiliary equipment. Reduced pressure and temperature steam can be returned for heat recovery.

Cooling in the ammonia and fertilizer production process can be done with condensate and chill water loops in the polygeneration process.

Excess gases produced as a byproduct of the various reactions described herein can be recovered and sold. For example, nitrogen produced by air separation unit 180, and supplied to heat exchanger 184, can be used for cooling and for the production of ammonia. Excess nitrogen can be sold or can be vented. Inert gases can be stripped by air separation unit 180, such as argon, can be sold or vented, if below emission limits.

In certain embodiments, water returning to the condensate system can optionally be diverted to the hydrogen generator 206 via line 202. Oxygen produced by hydrogen generator 206 can be supplied to oxygen-fired industrial process 106 via line 208. Hydrogen produced by hydrogen generator can be supplied to fourth reactor 214 for the production of ammonia via line 212. Excess water supplied to hydrogen generator 206 can be recovered via line 210.

In one aspect, the present invention utilizes the air separation unit cold box effluent gases as heat sinks for cooling of hot effluent exhaust gases from an oxygen-fired process. While described herein as an aspect of the invention utilizing oxygen-fired exhaust gases for the feedstock in the production of urea and other nitrogen based fertilizers, it is understood that the use of air separation unit gases as heat sinks to provide cooling can be applied to any process requiring cooling, and that the urea production described herein is just one example. For example, the air separation unit gases can also be used for integrated gasification combined cycle power plants which are oxygen-fired. Cooling of the discharge steam or gas treatment heat exchangers can be done with chilled water or with cold box effluent gases of the air separation passing through heat exchangers, thus eliminating the need for the external cooling water for evaporative cooling or air cooled condensers. In certain embodiments, any air separation unit situated near a power plant or steam process needing cooling can be utilized such that the air separation unit cold box gases provide a heat sink, thereby preventing water consumption that impacts the environment, or alternatively preventing requirements of extra energy use for air cooled heat exchangers, and capital and materials cost of extremely large equipment needed to provide this alternative cooling.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present invention.

I claim:

1. A method for the production of ammonia from exhaust flue gases of an oxygen-fired process, the method comprising the steps of:

supplying a hydrocarbon or carbonaceous feedstock and oxygen to an oxygen-fired process to produce an exhaust flue gas, said exhaust flue gas comprising carbon dioxide, carbon monoxide, and hydrogen;

supplying the exhaust flue gas to a first reactor, said first reactor comprising a catalyst and being configured to convert at least a portion of the carbon monoxide to carbon dioxide and produce a modified exhaust flue gas;

supplying the modified exhaust flue gas to a second reactor, said second reactor comprising a catalyst and being configured to convert at least a portion of the remaining carbon monoxide to carbon dioxide to produce a carbon dioxide containing flue gas;

supplying the carbon dioxide containing flue gas from the second reactor to a first condenser to remove water and produce a gas stream containing between 65-80 mol. % hydrogen, between 20-35.mol. % carbon dioxide and between 0-2 mol. % carbon monoxide;

supplying the gas stream from the first condenser to a carbon dioxide stripper to produce a hydrogen stream and a high purity carbon dioxide stream, wherein said carbon dioxide stripper being charged with a solvent suitable for extracting carbon dioxide, said hydrogen stream contains at least 95 mol. % hydrogen, and said high purity carbon dioxide stream contains at least 99 mol. % carbon dioxide;

supplying the hydrogen stream to a third reactor, said third reactor comprising a catalyst and being configured for production of methane from remaining amounts of carbon monoxide and carbon dioxide present in the hydrogen stream, said third reactor producing a methane product stream and a high purity hydrogen stream containing at least 99.9 mol. % of hydrogen;

supplying the high purity hydrogen stream from the third reactor and nitrogen gas from an air separation unit to a fourth reactor, said fourth reactor comprising a catalyst and being configured to produce an ammonia product stream;

supplying the high purity carbon dioxide stream from the carbon dioxide stripper and the ammonia from the fourth reactor to a fifth reactor, said fifth reactor being configured to produce a product stream comprising urea.

2. The method of claim 1, wherein the hydrocarbon feedstock is selected from methane or syngas.

3. The method of claim 1, wherein the oxygen has a purity of at least 99%.

4. The method of claim 3, further comprising separating nitrogen and oxygen from air with an air separation unit, and wherein the nitrogen is supplied to the fourth reactor and oxygen is supplied to the oxygen-fired process.

5. The method of claim 1, further comprising supplying hydrogen from a hydrogen generator to the oxygen-fired process with the hydrocarbon feedstock and oxygen to produce the exhaust flue gas.

6. The method of claim 1, further comprising the step of supplying the high purity hydrogen stream from the third reactor to a second condenser, said second condenser being configured to remove any trace water present in the high purity hydrogen stream.

7. The method of claim 6, further comprising the step of supplying water recovered from the first and second condensers to the hydrogen generator as feedstock.

8. The method of claim 1, further comprising the step of treating the hydrocarbon or carbonaceous feedstock to remove sulfur prior to being supplied to the oxygen-fired process.

9. The method of claim 1, further comprising the step of treating the exhaust flue gas to remove sulfur prior to being supplied to the first reactor.

10. The method of claim 9, wherein the sulfur is removed by treatment of the exhaust flue gas with a desulfurization agent selected from the group consisting of dry limestone, wet limestone, solvent, and amine solution.

11. The method of claim 1, wherein the oxygen supplied to the oxygen-fired process has a purity of at least about 99 mol. %.

12. The method of claim 1, wherein the oxygen supplied to the oxygen-fired process has a purity of at least about 99.9 mol. %.

13. The method of claim 1, wherein ratio of the hydrogen and the carbon dioxide in the exhaust flue gas is between about 2:1 and 4:1.

14. The method of claim 1, wherein ratio of the hydrogen and the carbon dioxide in the exhaust flue gas is between about 2.5:1 and 3.5:1.

15. The method of claim 1, wherein ratio of the hydrogen and the carbon dioxide in the exhaust flue gas is between about 2.9:1 and 3.1:1.

16. The method of claim 1, wherein the exhaust flue gas contains between about 60 and 65 mol. % hydrogen, between 17 and 23 mol. % carbon dioxide, and between 10 and 15 mol. % carbon monoxide.

17. The method of claim 1, wherein the solvent in the carbon dioxide stripper is an amine-based solution.

18. The method of claim 1, wherein the oxygen-fired process is carried out in non-catalytic partial oxidation reactor.

* * * * *